United States Patent [19]

Röder et al.

[11] 3,951,744

[45] Apr. 20, 1976

[54] PURIFICATION OF DEHYDROGENASES

[75] Inventors: Albert Röder, Seeshaupt; Klaus Beaucamp; Günter Weimann, both of Tutzing, Upper Bavaria; Walter Schneider, Weilheim; Klaus Mühlegger, Weilheim am Schleiferhausl, all of Germany

[73] Assignee: Boehringer Mannheim G.m.b.H., Mannheim-Waldhof, Germany

[22] Filed: July 16, 1974

[21] Appl. No.: 489,792

[30] Foreign Application Priority Data

July 23, 1973 Germany............................ 2337312

[52] U.S. Cl. ........................ 195/66 R; 195/103.5 C
[51] Int. Cl.² ........................................... C07G 7/02

[58] Field of Search ................................. 195/66 R

[56] References Cited
UNITED STATES PATENTS 3,810,823  5/1974  Fujii et al. ......................... 195/66 R

*Primary Examiner*—Lionel M. Shapiro
*Attorney, Agent, or Firm*—Burgess, Dinklage & Sprung

[57] ABSTRACT

NADP-dependent dehydrogenases are separated and purified by subjecting mixtures containing it to affinity chromatography using as the affinity chromatography material a nucleotide with a phosphate group in the 2'- or 3'-position, bound to a solid carrier.

13 Claims, No Drawings

PURIFICATION OF DEHYDROGENASES

This invention relates to a process for the isolation and purification of dehydrogenases.

Dehydrogenases play an important part in many enzymatic analytical processes. In particular, NADP-dependent enzymes, such as glucose-6-phosphate-dehydrogenase (G6P-DH) are used in clinical laboratories for the very important determination of glucose. Therefore, there is a need for a simple method for the isolation of these enzymes.

There are essentially two methods for the enzymatic determination of glucose. For routine use in the clinical laboratory, the process using glucose oxidase and a compound which gives a color reaction with hydrogen peroxide has proved to be satisfactory.

However, for extremely high accuracy requirements, it is preferable to use the enzymes hexokinase and glucose-6-phosphate-dehydrogenase (see, for example H. U. Bergmeyer, E. Bernt, F. Schmidt and H. Stork, in H. U. Bergmeyer's "Methoden der enzymatischen Analyse," second edition, 1970, page 1163). However, the determination of blood sugar according to this method requires enzymes of high purity. Thus, the following enzymatic contaminants have an especially disturbing action: 6-phosphogluconate-dehydrogenase (6-PGDH), phosphoglucomutase (PGluM), hexokinase (HK), phosphoglucose-isomerase (PGI) and glutathionereductase (GR). Their presence would uncontrollably falsify the glucose analysis values. If the sample to be analyzed, for example human serum, contains adenosine triphosphate (ATP) and glucose, as well as glucose-6-phosphate (G6P), then an exact analysis of both substrates side-by-side is not possible when the G6P-DH is contaminated with hexokinase. Comparable difficulties arise in the case of the presence of the other foreign enzymes mentioned in the G6P-DH, such as for example of PGI, since fructose would here also react, of GR, since the glutathione in the sample would also be included, and of 6-PGDH, since it would react further with the reaction product of the G6P determination and would stimulate too high values.

In order to remove the mentioned foreign activities, a laborious and expensive isolation process is necessary. Thus, in a process described by L. Glaser and D. H. Brown (J.B.C., 216, 67/1955), the following steps are employed for the purification of G6P-DH from yeast: autolysis, protamine precipitation, ammonium sulfate fractionation, dialysis, calcium phosphate gel adsorption, dialysis; ethanol fractionation, aluminum oxide adsorption, starch-cellite adsorption, ammonium sulfate separation, ribonucleic acid. However, even with this process, it was not possible to remove residual traces of hexokinase. In addition, the yields were low (19 percent).

S. A. Kuby and E. A. Noldman have described a process (Meth. in Enzym., 9, 160/1969) which is also extremely laborious (see also J. Biol. Chem., 36, 1225/1961) which, via 17 steps, gives only a low yield of an apparently pure preparation. In the case of this process, a yeast extract is first prepared, followed by an ammonium sulfate (AS) fractionation, subsequently a silver nitrate precipitation, an extraction with ethylenediaminetetraacetic acid (EDTA) and a further ammonium sulfate fractionation. After dialysis, there is carried out an ethanol fractionation, a bentonite adsorption, another ammonium sulfate fractionation and subsequently a dialysis, followed by an acetone precipitation and another ammonium sulfate precipitation; after a dialysis, there follows a diethylaminoethyl-cellulose adsorption, another dialysis and a second diethylaminoethyl-cellulose adsorption, an ammonium sulfate precipitation, a sulfate fractionation and three recrystallizations. This process is not only extraordinarily laborious and expensive but also cannot be carried out on a large scale in batches of any desired size.

Not one of the known processes is able to satisfy the need for a simple, reproducible enrichment process for G6P-DH. In particular, it was also not possible to isolate the two enzymes G6P-DH and HK from one and the same batch.

For overcoming the above-mentioned difficulties and disadvantages, attempts have already been made to purify dehydrogenases by the affinity chromatography principle. A process of this type, which utilizes the alternating action between coenzyme and enzyme, in that the co-enzyme of the enzyme to be purified is fixed on a solid carrier, has been described for the dehydrogenases by C. R. Lowe and P. D. G. Dean (see FEBS Letters, 14, 313/1971). The use of this process has also been suggested for the purification of G6P-DH in German Pat. No. 2,206,636. However, this process only gives an approximately 20-fold enrichment (cf. J. D. Hocking and J. I. Harris, Biochem. J., 1972). Although this process provides a certain degree of advance, it is not really a simple process for the purification of dehydrogenases because the enrichment which can be achieved is much too low for the preparation of very pure enzymes and, therefore, the known, old and laborious methods must still be additionally employed.

The present invention substantially overcomes the above-described disadvantages and provides a very effective and simple process for the purification of dehydrogenases, especially of G6P-DH, which enables very pure enzymes to be obtained in a substantially simpler manner and thus makes enzymes available for a wider field of use.

Essentially, the process of the invention comprises separating and purifying NADP-dependent hydrogenases, such as G6P-DH, with the use of affinity chromatography using as the affinity material a nucleotide with a phosphate group in the 2'- or 3'-position, bound to a solid carrier.

The process according to the present invention permits, in a single step, an extraordinarily high enzyme enrichment of up to 700-fold. Since, with the natural co-enzyme, which must be regarded as being by far the most favorable acceptor group on a carrier, enrichments of only up to 20-fold can be achieved, this result is extremely surprising because, with an acceptor group which is relatively distant from the natural co-enzyme, such as is used in the process according to the present invention, a substantially poorer result was to have been expected than with the use of the natural co-enzyme as acceptor which exhibits a maximum affinity to its apoenzyme and permits a freeing of the affinity chromatography material in which an inactivation of the enzyme must not be provided for.

The carrier material used according to the present invention can be a natural or synthetic material. It is preferred to use a hydrophilic carrier material, for example, polyacrylamide, a polymer with free hydroxyl groups, for example, cellulose, starch, dextran or agarose or a chemical conversion product thereof, polyvinyl alcohol, or an insolubilized protein. There can also be used a polyamide or a polyester or a polystyrene derivative, as well as an inorganic carrier material, for example glass. The carrier material can be in the form of pearls or granulates or of a fabric or can be embedded, in a supporting material. Very good results are achieved with a carrier material in the form of permeable pearls or granulates which can be used not only in a column but also in a batch process. Especially preferred carrier materials are crosslinked dextran and agarose.

The grouping used in the process according to the present invention as acceptor consists of a nucleotide with a phosphate group in the 2'- or 3'-position. These compounds can be represented by the following formula:

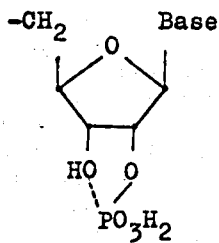

The bonding of this acceptor molecule can take place not only via the $CH_2$ group of the sugar but also via the base. The bonding can take place directly or via a bridging grouping. The nature of this binding is unimportant for the principle of the process according to the present invention but, in individual cases, the result of the process can be influenced thereby to a certain extent. Therefore, in order to achieve, in a particular case, an optimum enrichment of a particular enzyme, it is expedient to try out various types of binding in order to obtain the best enrichment effect.

As bases present in the acceptor grouping, there can, within the scope of the process according to the present invention, be used not only the natural bases occurring in nucleotides, for example, uridine, guanosine, adenosine, thymidine, cytidine, xanthene, methyl-xanthene and the like, but also the substituted derivatives and homologs thereof.

For binding the acceptor to the carrier, there can be used the known chemical bonding methods. The nature of the binding is, however, not the subject of the present invention. Examples of known methods include, for example, activation with cyanogen bromide, coupling with a p-aminophenyl grouping, with aminocaproic acid, aminoethylamidosuccinic acid and the like.

Other examples of known coupling methods for bonding the acceptor to the carrier are the introduction of groups like azide- or chloro- Arizinyl-groups which are subsequently reacted with acceptor. In the case of carrier materials containing amino groups or carboxyl groups, coupling can, for example, also take place with the use of carbodiimides.

As mentioned above, the process according to the present invention can be used for the separation and purification of NADP-dependent dehydrogenases. Amongst the NADP-dependent dehydrogenases, there are also to be understood, within the scope of the present invention, those dehydrogenases which are dependent not only upon NADP alone but also upon NAD. Examples of NADP-dependent dehydrogenases which can be purified by the process according to the present invention are, apart from G6P-DH, which is preferred, also glutamate dehydrogenase, isocitrate, dehydrogenase, glutathione-reductase, glyceraldehyde-3-phosphatedehydrogenase, 6-phosphogluconic acid-dehydrogenase, lactatedehydrogenase and malate-dehydrogenase.

Surprisingly, the various NADP-dependent dehydrogenases exhibit various affinities to the various acceptors which can be used according to the present invention so that the process of the present invention can also be used for the separation of individual NADP-dependent dehydrogenases from another. The dehydrogenases which can be isolated and purified according to the process of the present invention include crude enzyme extracts and enzyme mixtures which originate from animal, vegetable or microbiological tissues.

The process according to the present invention is preferably carried out by allowing a solution which contains the desired dehydrogenase, for example as the component of an enzyme or protein mixture, to pass through a column which is filled with the chromatographic material used according to the present invention. After washing the column for the removal of undesired accompanying materials, the adsorbed enzymes are then eluted, preferably with the use of buffer solutions with increasing ionic strength, i.e., by gradient elution. Especially good results have been obtained with inorganic phosphate buffer solutions but other buffer solutions which do not denature the desired enzyme can also be used. Furthermore, neutral salt solutions, for example solutions of sodium chloride or of ammonium sulfate, can be used. Finally, the elution can also be carried out with the co-enzyme, substrate or an inhibitor. Instead of a column, the process according to the present invention can also be carried out by adsorption and elution in a batch process.

As already mentioned, the process according to the present invention permits an extraordinarily substantial purification and enrichment of the desired enzymes in a single process step. The process according to the present invention is extraordinarily specific and uncomplicated and can be carried out very quickly. Since a several-100-fold purification is possible in a single step, it is usually sufficient to carry out the process according to the present invention once in order to obtain an enzyme preparation of sufficient purity for practical purposes. However, for special purposes, the process according to the present invention can be repeated, preferably with the use of different affinity chromatography materials. Finally, it is also possible further to purify dehydro genases purified by the process according to the present invention, using methods known for the high purification of enzymes of this type.

In the following Examples, which are given for the purpose of illustrating the present invention, the following abbrevations are employed:

| | |
|---|---|
| APUP | = 5'-(p-aminophenylphosphoryl)-uridine-2'(3')-phosphate |
| APGP | = 5'-(p-aminophenylphosphoryl-guanosine-2'(3')-phosphate |
| APAP | = 5'-(p-aminophenylphosphoryl)-adenosine-2'(3')-phosphate |

| | |
|---|---|
| APG | = 5'-(p-aminophenylphosphoryl)-guanosine |
| APA | = 5'-(p-aminophenylphosphoryl)-adenosine |
| 8-AD-A-5-MP | = 8-aminoethylaminoadenosine-5'-phosphate B |
| ACS-APG | = APG coupled to agarose-aminocaproic acid |
| GDA-APG | = APG coupled to agarose-aminoethylamido-succinic acid |
| 8-HMD-A-5-MP | = 8-aminohexylaminoadenosine-5'-phosphate B |
| 8-HMD-A-2,5-DP | = 8-aminohexylaminoadenosine-2'(3'),5'-phosphate B |
| GlDH | = glutamate-dehydrogenase |
| ICDH | = isocitrate-dehydrogenase |
| GR | = glutathione-reductase |
| GAPDH | = glyceraldehyde-3-phosphate-dehydrogenase |
| 8-HMD-A-2',3'-P | = 8-aminohexylaminoadenosine-2'(3')-phosphate |
| LDH | = lactate dehydrogenase |
| MDH | = malate-dehydrogenase |
| PGK | = 3-phosphoglycerate-kinase |
| HK | = hexokinase |
| GK | = glycerokinase |
| AS | = ammonium sulfate |
| CK | = creatinine kinase |
| MK | = myokinase |
| PK | = pyruvate kinase |

The method of writing the base as 2'(3') means that the phosphate group is in the 2'- or 3'-position but the precise position has not been determined. Mixtures are probably present. B indicates that the acceptor is bound via the 8-position of the base to the carrier.

EXAMPLE 1

A. Preparation of the affinity adsorbent 500 g suction-filtered agarose (Sepharose 4Bd of the firm Pharmacia, Uppsala, Sweden) were slurried in 500 ml distilled water. In addition, 50 g cyanogen bromide were dissolved in distilled water. The agarose was then adjusted to pH 11 with 5N aqueous sodium hydroxide solution and the dissolved cyanogen bromide added thereto. By the addition of 5N aqueous sodium hydroxide solution, the pH was maintained at about 11 for 10 minutes. Thereafter, the activated agarose was filtered off with suction and thoroughly washed with 0.5M ice-cold aqueous dipotassium hydrogen phosphate solution. It was subsequently coupled with the acceptor to be fixed (5 g in 1000 ml 0.5M aqueous dipotassium hydrogen phosphate solution) at pH 9 overnight at 4°C. The finished carrier was finally washed free of inhibitor with one liter amounts of 0.5M aqueous dipotassium hydrogen phosphate solution, distilled water, 0.1M acetic acid, distilled water, 1.0M aqueous sodium chloride solution and distilled water. The content of the affinity adsorbent thus prepared was between about 5 and 10 μmol acceptor per g on a gel filtered off with suction on a glass frit.

B. Adsorption of G-6-P-DH from yeast autolysate

Starting from 285 g dry yeast, the precipitate obtained by AS fractionation at an AS concentration of 1.6-2.6M was dissolved and dialyzed against water. To 500 ml dialysate with a specific G6P-DH activity of 0.6 were subsequently added 25 g APGP-agarose, prepared according to A above, using APGP as acceptor. After stirring for twenty minutes, the material was filtered off with suction. The supernatant still contained 8.6% of the G-6-P-DH initially used. After washing the adsorbent with 0.4M aqueous sodium chloride solution, 60 percent of the G-6-P-DH was subsequently eluted with 0.5M phosphate at a pH of 7.6. There was obtained a specific activity of 96. The enzyme also contained the following foreign activities: ADH 0.26%, HK 0.22%, PGluM 0.02%, PGJ 0.12%, GR 0.37%, 6PGDH 1.46%.

EXAMPLE 2

Chromatography of G-6-P-DH from a yeast autolysate after a positive AS precipitation:

Starting from 950 g dry yeast, after 5 hours fermentation, the precipitate of the ammonium sulfate precipitation obtained as described in Example 1B was dissolved in and dialyzed against water. The dialysate was diluted to 5 liters (20 mg protein/ml) and chromatographed over 150 g APGP-agarose. After washing with 0.4M aqueous sodium chloride solution, the G-6-P-DH was eluted with 1M ammonium sulfate solution in a yield of about 80% with a specific activity of 420 and with the following contents of foreign activities: 6PGDH 0.04%, PGJ 0.01%, HK 0.08%, GR 0.01%, PGluM 0.01% and ADH 0.01%.

The following Table I summarizes the results obtained:

TABLE I

| Step | Specific Activity | Yield as Activity in % | Purification Factor |
|---|---|---|---|
| autolysis | | | |
| AS fractionation | | | |
| dialysis | 0.6 | 100 | |
| chromatography | 420 | 80 | 700 |

EXAMPLE 3 (COMPARISON EXAMPLE)

The following Table contains the results of the process for the isolation of G-6-P-DH according to the method of S. A. Kuby and E. A. Noltmann, Colowick-Kaplan, Methods in Enzymology, 9, 116 et seq./1966:

TABLE II

| Step | Specific Activity | Yield as Activity in % | Purification Factor |
|---|---|---|---|
| autolysis | 0.16 | 100 | |
| AS fractionation | 0.20 | 90 | 1.2 |
| silver nitrate precipitation, extraction of the precipitate | 0.5 | 70 | 2.5 |
| AS fractionation | 0.7 | 65 | 1.4 |
| ethanol fractionation | 13 | 56 | 18 |
| bentonite adsorption | 22 | 46 | 1.7 |
| AS fractionation | 37 | 42 | 1.5 |
| acetone fractionation | 71 | 34 | 2.1 |
| AS fractionation | 106 | 27 | 1.5 |

TABLE II-continued

| Step | Specific Activity | Yield as Activity in % | Purification Factor |
|---|---|---|---|
| dialysis, DEAE-cellulose | 160 | 23 | 1.5 |
| AS fractionation | 200 | 21 | 1.2 |
| various crystallisations | 410 | 10 | |

EXAMPLE 4

Isolation of G-6-P-DH from yeast autolysate by direct chromatography:

500 g dry yeast were autolyzed at 37°C for twenty hours in 1.2 liters 0.025M aqueous disodium hydrogen phosphate solution at pH 5. The autolysate was diluted with 3.0 liters ice-cold water and 4.5 percent polyethyleneimine was added, followed by centrifuging and centrifugate was chromatographed on 150 g APGP-agarose. Starting from a specific activity of about 0.4 U/mg, there was obtained, after elution with 1M aqueous ammonium sulfate solution, in a yield of 83% of theory, 66 mg G-6-P-DH with a specific activity of 174. The degree of enrichment was about 435 fold.

EXAMPLE 5

Isolation of G-6-P-DH from fresh yeast extract.

Fresh yeast was digested in a glass ball mill. From 1.5 kg fresh yeast, which had been suspended in 10 liters tap water, there was obtained, after the addition of 1 percent polyethyleneimine and centrifuging, a clear centrifugate. 6.5 liters of this centrifugate were chromatographed on a column containing 100 g APGP-agarose. After thorough washing with 0.4M aqueous sodium chloride solution, 84 percent of the G-6-P-DH activity was eluted with 1M aqueous ammonium sulfate solution (50 mg, specific activity = 264). The preparation did not contain PGI or ADH but contained 0.1%, GR, 0.01% HK and 0.02% and 6PGDH.

Results analogous to those given in the above Examples were obtained when eluting with 0.1M aqueous citrate buffer of pH 6, 1M aqueous sodium chloride solution, 0.3M aqueous magnesium chloride solution, 0.1M aqueous pyrophosphate buffer of pH 6.5 or 0.3M aqueous phosphate buffer of pH 7.6.

EXAMPLE 6

This Example illustrates the adsorption of G6P-DH (specific activity about 150) on agaroses which contain various acceptors. The acceptors were all bound after the cyanogen bromide activation. The loading (amount of acceptor per g of carrier) was about 5 – 10 μmol/g. 5 ml amounts of enzyme solution with a concentration of 1 mg/ml were applied thereto. To this enzyme solution were added 500 mg acceptor-containing agarose. The following Table III indicates the acceptors used and the results obtained therewith.

TABLE III

| acceptor | % bound |
|---|---|
| according to the invention: | |
| APUP | 75 |
| APGP | 95 |
| APAP | 95 |
| 8-HMD-A-5-MP | 62 |
| 8-HMD-A-2,5-DP | 97 |
| comparison: | |
| APG | 8 |
| APA | 0 |
| 8-AD-A-5-MP | 15 |
| ACS-APG | 20 |
| GDA-APG | 20 |

The acceptors not according to the present invention, i.e., which do not contain a phosphate group in the 2'- or 3'-position, such as APG and APA, as well as those in which the phosphate group is in the 5'-position, such as 8-AD-A-5-MP, ACS-APG and GDA-APG, are, as the above results show, unsuitable for the purification of dehydrogenases.

EXAMPLE 7

Chromatography of G6P-DH from yeast dialysate on APUP-agarose.

3.2 liters yeast dialysate, obtained in the manner described in Example 2, were diluted to eight liters (20 mg protein/ml, $1.1 \times 10^5$ U). This solution was chromatographed on 0.5 kg APUP-agarose (column dimensions $5 \times 32$ cm). Elution was carried out with 0.25M phosphate (pH 7.6). The yield was 200 mg with 320 U/mg (corresponding to 58%).

EXAMPLE 8

Chromatography of G6P-DH from dried yeast on APUP-agarose.

460 g dried yeast were autolyzed in 1.2 liters 0.2M sodium phosphate buffer for six hours at 37°C and pH 6.5. Subsequently, the autolysis product was diluted with ice water 1:4 and the cell residues were precipitated by the addition of 1 percent polyethyleneimine. The centrifugate thereof contained $3.1 \times 10^4$ U (specific activity 0.55). After dilution to 21 liters, the enzyme solution was chromatographed on 200 g APUP-agarose. After washing with 0.15M aqueous sodium chloride solution, the G6P-DH was eluted with 0.25M phosphate (pH 7.6). The yield was 76% (223 mg, specific activity 105, 0.02% HK, 0.04% GR, 0.4% 6-PG-DH). The total yield was 42 mg with a specific activity of 380; the enrichment was about 700 fold.

EXAMPLE 9

Chromatography of G6P-DH from fresh yeast on APUP-agarose.

1.5 kg fresh yeast were slurried in 10 liters water and digested in a glass bead mill. After the addition of 1 percent polyethyleneimine and centrifuging off the precipitate, there were obtained 8.5 liters of filtrate which contained $1.9 \times 10^4$ U (100%). This was chromatographed on a 200 g APUP-agarose column. The eluate obtained by elution with 0.25M phosphate buffer (pH 7.6) contained 91 percent (265 mg, specific activity 63). The content of foreign activities was 0.33% 6-PG-DH, 0.02%, HK and 0.03% GR.

EXAMPLE 10

Various NADP-dependent dehydrogenases were adsorbed on APGP-agarose. In each case, 500 mg of acceptor-containing agarose were added to 5 ml of enzyme solution with a content of 1 mg/ml. The following Table IV shows the enzymes used, the percentage adsorption thereof on the chromatographic material under comparable conditions, as well as the percentage elution upon washing with a 0.05M aqueous solution of sodium chloride.

TABLE IV

| enzyme | % adsorption under comparable conditions | elution upon washing with 0.05M aqueous sodium chloride solution |
|---|---|---|
| G6P-DH | 95 | 0 |
| 6PG-DH | 87 | 0 |
| GlDH | 87 | 0 |
| ICDH | 100 | 0 |
| GR | 95 | 5 |
| GAPDH | 99 | 14 |
| MDH | 99 | 5 |

EXAMPLE 11

Separation of 6PG-DH as foreign activity from α-glucosidase on HMD-A-2'(3')-phosphate-agarose.

30 mg of an α-glucosidase with a specific activity of 40 U/mg, containing 0.52 percent 6PG-DH as impurity, were dissolved in 6 ml 0.1M citrate buffer (pH 6.5) and this solution was chromatographed on a 1 × 8 cm column containing 6 g HMD-A-2'-(3')-phosphate-agarose. The α-glucosidase was not bound and, upon washing the column with an amount of the citrate buffer equal to twice the volume of the column, was recovered in a yield of 93.7 percent. The content of 6PG-DH was 0.0017 percent.

EXAMPLE 12

Aqueous bovine liver extract was mixed with 10 percent polyethyleneimine. Glutamate-dehydrogenase was adsorbed from the centrifugate (specific activity 3.5 U/mg) on APUP agarose (capacity 4.2 mg/ml adsorbent). After washing with 0.15M aqueous sodium chloride solution, the enzyme was eluted with 1M phosphate buffer (pH 6.8), which was 1M with regard to sodium chloride, the yield being 66.7 percent and the degree of purification 34 fold.

It will be understood that the specification and examples are illustrative but not limitative of the present invention and that other embodiments within the spirit and scope of the invention will suggest themselves to those skilled in the art.

What is claimed is:

1. Process for the separation and purification of NADP-dependent dehydrogenases which comprises subjecting the dehydrogenase to chromatography using as the affinity chromatography material a nucleotide with a phosphate group in the 2'- or 3'-position, bound to a solid carrier material.

2. Process as claimed in claim 1 wherein the nucleotide is uridine-2'(3')-phosphate.

3. Process as claimed in claim 1 wherein the nucleotide is guanosine-2'(3')-phosphate.

4. Process as claimed in claim 1 wherein the nucleotide is thymidine-2'(3')-phosphate.

5. Process as claimed in claim 1 wherein the nucleotide is cytidine-2'(3')-phosphate.

6. Process as claimed in claim 1 wherein the nucleotide is xanthine-2'(3')-phosphate.

7. Process as claimed in claim 1 wherein the nucleotide is methylxanthine-2'(3')-phosphate.

8. Process as claimed in claim 1 wherein the nucleotide is adenosine-2'(3')-phosphate.

9. Process as claimed in claim 1 wherein the carrier material is a hydrophilic carrier material.

10. Process as claimed in claim 9 wherein the hydrophilic carrier material is a cross-linked dextran or agarose.

11. Process as claimed in claim 1 wherein the dehydrogenase is eluted from the carrier by gradient elution.

12. Process as claimed in claim 11 wherein elution is carried out with an inorganic phosphate buffer solution or with a neutral salt solution.

13. Process as claimed in claim 1 wherein the carrier used is packed in a column.

* * * * *